United States Patent
Weed et al.

(10) Patent No.: US 11,769,628 B2
(45) Date of Patent: Sep. 26, 2023

(54) POWER COUPLING DEVICE

(71) Applicant: Analogic Corporation, Peabody, MA (US)

(72) Inventors: Steven Dana Weed, Marblehead, MA (US); Patrick Richard Splinter, Kingston, MA (US); Matthew Hanlon, Kingston, MA (US); Santosh Arcot, Shrewsbury, MA (US)

(73) Assignee: Analogic Corporation, Peabody, MA (US)

( * ) Notice: Subject to any disclaimer, the term of this patent is extended or adjusted under 35 U.S.C. 154(b) by 809 days.

(21) Appl. No.: 16/322,907

(22) PCT Filed: Aug. 3, 2016

(86) PCT No.: PCT/US2016/045250
§ 371 (c)(1),
(2) Date: Feb. 1, 2019

(87) PCT Pub. No.: WO2018/026359
PCT Pub. Date: Feb. 8, 2018

(65) Prior Publication Data
US 2019/0173315 A1 Jun. 6, 2019

(51) Int. Cl.
*H01F 38/18* (2006.01)
*H01F 27/30* (2006.01)
(Continued)

(52) U.S. Cl.
CPC ............ *H01F 38/18* (2013.01); *A61B 6/032* (2013.01); *A61B 6/56* (2013.01); *H01F 3/10* (2013.01);
(Continued)

(58) Field of Classification Search
CPC ........ H01F 38/18; H01F 3/10; H01F 27/2823; H01F 27/306; H02J 50/10; A61B 6/032
See application file for complete search history.

(56) References Cited

U.S. PATENT DOCUMENTS

| 8,350,655 B2 | 1/2013 | Dobbs |
| 2006/0022785 A1 | 2/2006 | Dobbs |

(Continued)

FOREIGN PATENT DOCUMENTS

| CH | 700533 A1 | 9/2010 |
| CN | 103155060 A | 6/2013 |

(Continued)

OTHER PUBLICATIONS

Chinese First Office Action for Chinese Application No. 201680088332.7, dated May 26, 2020, 16 pages with translation.
(Continued)

*Primary Examiner* — Carlos Amaya
(74) *Attorney, Agent, or Firm* — TraskBritt

(57) ABSTRACT

One or more techniques and/or systems described herein provide a power coupling device, such as may be used to transfer power between a stator and a rotor. The power coupling device includes a support structure defining an opening. The power coupling device includes a core element including a ferrite material. The core element is received within the opening of the support structure. The core element defines a core channel. The power coupling device includes an inductive element that is received within the core channel. The power coupling device includes an attachment structure removably attached to the support structure. The attachment structure attaches the core element to the support structure. The core element is disposed between the support structure and the attachment structure.

18 Claims, 9 Drawing Sheets

(51) Int. Cl.
*A61B 6/03* (2006.01)
*A61B 6/00* (2006.01)
*H01F 3/10* (2006.01)
*H02J 50/10* (2016.01)
*H01F 27/28* (2006.01)

(52) U.S. Cl.
CPC ....... H01F 27/2823 (2013.01); H01F 27/306 (2013.01); H02J 50/10 (2016.02)

(56) References Cited

U.S. PATENT DOCUMENTS

| | | |
|---|---|---|
| 2010/0225433 A1 | 9/2010 | Dunlap et al. |
| 2011/0018667 A1* | 1/2011 | Jaeger ................. H01F 27/2804 336/120 |
| 2013/0187740 A1* | 7/2013 | Loiselle ................. H01F 38/18 336/120 |
| 2016/0203906 A1* | 7/2016 | Lange .................... H01F 27/24 336/119 |

FOREIGN PATENT DOCUMENTS

| | | |
|---|---|---|
| DE | 20208785 U1 | 10/2003 |
| DE | 102005009866 A1 | 9/2006 |
| WO | 2011/146067 A1 | 11/2011 |
| WO | 2012/166134 A1 | 12/2012 |
| WO | 2015/019478 A1 | 2/2015 |

OTHER PUBLICATIONS

Chinese Search Report for Chinese Application No. 201680088332.7, dated May 19, 2020, 2 pages.
Written Opinion of the International Searching Authority forPCT Application No. PCT/US2016/045250 dated Jul. 3, 2017, 17 pages.
International Search Report for PCT Application No. PCT/US2016/045250 dated Jul. 3, 2017, 7 pages.
Chinese Second Office Action for Chinese Application No. 201680088332.7, dated Mar. 26, 2021, 15 pages with translation.
European Communication pursuant to Article 94(3) EPC for European Application No. 16758003.4, dated Dec. 3, 2019, 9 pages.
Chinese First Office Action and Search Report for Chinese Application No. 202011038560.8, dated Jan. 18, 2022, 9 pages with English translation.
European Communication pursuant to Article 94(3) EPC for European Application No. 16758003.4, dated Dec. 16, 2021, 7 pages.
Chinese Notification of Reexamination for Chinese Application No. 201680088332.7, dated Jun. 24, 2022, 15 pages with translation.
Reexamination Decision for Chinese Application No. 201680088332.7, dated Dec. 13, 2022, 41 pages.

* cited by examiner

POWER COUPLING DEVICE

CROSS-REFERENCE TO RELATED APPLICATION

This application is a national phase entry under 35 U.S.C. § 371 of International Patent Application PCT/US2016/045250, filed Aug. 3, 2016, designating the United States of America and published in English as International Patent Publication WO 2018/026359 A1 on Feb. 8, 2018, the disclosure of which is hereby incorporated herein in its entirety by this reference.

BACKGROUND

The present application relates to a power coupling device configured to transfer power between a rotating unit (e.g., a rotor) and a stationary unit (e.g., a stator) and/or between two rotating units. It finds particular application in the context of computed tomography (CT) scanners, such as might be used in medical, security, and/or industrial applications. For example, the power coupling device may be configured to transfer power from a stationary unit to a rotating unit that houses a radiation source and a detector array. However, the features described herein are not intended to be limited to CT applications and/or other imaging applications.

Systems that comprise electronic components within a rotating unit often require power to be provided to the rotating unit via a power coupling apparatus. For example, in CT scanners, power is supplied to electronics on a rotating unit of the CT scanner using a power coupling device. Traditionally, these power coupling devices have been slip-ring/brush assemblies. Slip-rings transfer power between a stationary unit and a rotating unit (e.g., or between two rotating units), through the contact of two materials (e.g., via a sliding contact). Slip-ring assemblies typically comprise two or more continuous conducting rings and one or more brushes on respective rings for delivering current to and from the rings.

While the use of brushes and slip-rings has proven effective for supplying power to electronics comprised in a rotating unit, conventional brush and slip-ring mechanisms tend to be dirty, unreliable, and/or noisy. For example, the brushes can break down to create metallic dust overtime, which may cause problems with ultra-sensitive electronics. Moreover, in some applications, such as where sensitive diagnostic/imaging procedures are being performed (e.g., such as in CT imaging), the electric noise inherent in the power being transferred and/or generated by the brushes can cause interference with the procedures. Other drawbacks of slip-ring assemblies include the cost and complexity of manufacture due to the special materials and/or the mechanical precision that is generally required.

More recently, contactless assemblies have been proposed for transferring power between a stationary unit and a rotating unit in the context of radiation imaging. For example, U.S. Pat. No. 8,350,655, assigned to Analogic Corporation and incorporated herein by reference, describes one such contactless power coupling device for CT scanners and other radiation imaging devices. While these contactless power devices have solved many of the aforementioned drawbacks of slip-ring assemblies, these contactless power coupling devices are often costly to manufacture due to, among other things, their size requirements.

BRIEF SUMMARY

Aspects of the present application address the above matters, and others. According to one aspect, a power coupling device is configured to transfer power between a stator and a rotor. The power coupling device comprises a support structure defining an opening. The power coupling device comprises a core element comprising a ferrite material. The core element is configured to be received within the opening of the support structure. The core element defines a core channel. The power coupling device comprises an inductive element configured to be received within the core channel. The power coupling device comprises an attachment structure removably attached to the support structure. The attachment structure is configured to attach the core element to the support structure. The core element is disposed between the support structure and the attachment structure.

According to another aspect, a segmented power coupling device comprising a plurality of segments configured to transfer power between a stator and a rotor. The segmented power coupling device comprises a segment comprising a support structure defining an opening. The segment comprises a core element comprising a ferrite material and defining a first side and a second side. The core element is configured to be received within the opening of the support structure. The core element defines a core channel defined along the first side. The segment comprises an inductive element configured to be at least partially received within the core channel and wound around the core element from the first side to the second side.

According to yet another aspect, a power coupling device is configured to transfer power between a stator and a rotor. The power coupling device comprises a support structure defining a support member and an opening. The power coupling device comprises a core element comprising a ferrite material and configured to be received within the opening of the support structure. The core element defines a core channel and the support member of the support structure configured to be received within the core channel. The power coupling device comprises an inductive element configured to be received within the core channel. The support member of the support structure is disposed between the inductive element and the core element along a back face of the core element.

According to yet another aspect, a segmented power coupling device comprises a plurality of segments configured to transfer power between a stator and a rotor. The segmented power coupling device comprises a first subset of the plurality of segments arranged to define a ring. The first subset of the plurality of segments comprises a plurality of first inductive elements defining a first winding of a transformer. The segmented power coupling device comprises a second subset of the plurality of segments arranged to define a partial ring. The second subset of the plurality of segments comprises one or more second inductive elements arranged to define one or more additional windings of the transformer.

Those of ordinary skill in the art will appreciate still other aspects of the present application upon reading and understanding the appended description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
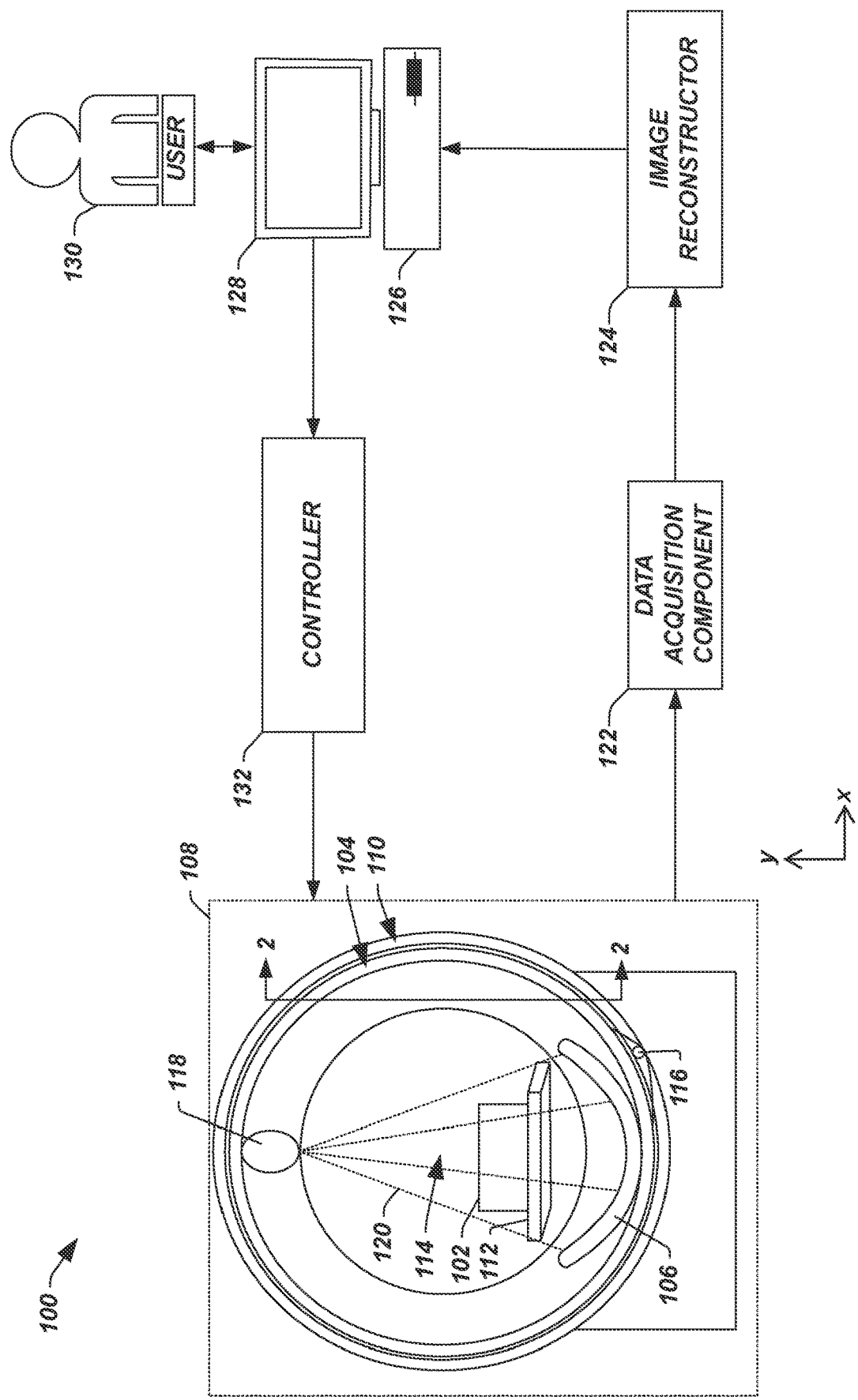
FIG. 1 is a schematic block diagram illustrating an example environment for using a power coupling device such as described herein.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a power coupling device that is configured to transfer power between a stator and a rotor. The power coupling device comprises a support structure that defines an opening. A core element, comprising a ferrite material, can be received within the opening of the support structure. The core element can define a core channel. An inductive element (e.g., a winding) can be received within the core channel. The inductive element may comprise electrically conductive wires, for example. An attachment structure may be removably attached to the support structure.

Accordingly, as described herein, the attachment structure can attach the core element to the support structure, such that the core element is maintained in a substantially fixed position with respect to the support structure. In this fixed position, the core element may be disposed between the support structure and the attachment structure. In an example, the attachment structure can be detached from the support structure, such that the core element can be separated and detached from the support structure.

It may be appreciated that in accordance with the aforementioned design, the inductive element and the core element may be secured or fixed in place by the attachment structure. Accordingly, little to no epoxy may be used in the manufacturing of the power coupling device. Moreover, as will be described in more detail below, the support structure may be manufactured using conductive or non-conductive materials. By manufacturing the support structure out of low cost materials, such as a polymer-based material, the cost of manufacturing (e.g., material costs, labor costs, etc.) may be reduced.

In some embodiments, the power coupling device may be divided into a plurality of segments that can transfer power between a stator and a rotor. Respective segments may comprise a support structure and a core element. Division of the power coupling device into segments may further reduce the cost of manufacturing due to the reduced size of the manufactured piece. In addition, one or more segments can be selectively removed and/or attached so as to allow for service to be provided to the segments.

Although the singular may be used herein for convenience in introducing terms such as "body," "object," "stator," "rotor," "airgap," "shield," "core," "winding," "center," "axis," etc., a similar situation will of course exist, and the present disclosure and/or claimed subject matter should be understood to, in general, be applicable where plurality or pluralities of one or more of such features is or are present. Conversely, where plurality or pluralities are discussed, this is not to necessarily exclude the singular. Also, with regard to usage of prepositions "between" and "among," except where otherwise clear from context, use of "between" is not intended to necessarily imply limitation to two objects, and use of "among" is not intended to necessarily imply limitation to more than two objects.

Note that the term "noncontact" is used herein to refer to the ability to transfer power in inductive fashion between or among bodies configured for relative rotation, and should not be understood to necessarily preclude possible contact between or among such bodies for other purposes, including, for example, electrostatic discharge, exchange or transmission of data, mechanical drive or support, braking and safety mechanisms, low-voltage power transfer, and/or high-voltage power transfer, etc. such as might be desired in addition to power transferred inductively by the types of power coupling devices disclosed herein.

It should also be noted that in the present specification, except where otherwise clear from context, the terms "gap" and "airgap" are used more or less interchangeably; although the term "airgap" may be used herein, as this should be understood to be mere deference to convention, it should be understood that such gaps are not limited to air, it being possible for vacuum, oil, and/or other fluid and/or gas, and/or sliding and/or roller bearings or other such contrivances permitting relative movement to completely or partially fill such spaces.

FIG. 1 is an illustration of an example environment 100 in which a power coupling device as described herein may be useful. More particularly, FIG. 1 illustrates an example computed tomography (CT) apparatus that can be configured to acquire volumetric information regarding an object 102 under examination and generate two-dimensional and/or three-dimensional images therefrom.

It will be appreciated that while a CT apparatus is described herein, the instant application is not intended to be so limited. That is, to the extent practical, the instant application, including the scope of the claimed subject matter, is intended to be applicable to other apparatuses that comprise a rotor (e.g., a rotating unit) and a stator (e.g., a stationary unit) and/or two rotating units over which power is transferred. Moreover, the example environment 100 merely illustrates an example schematic and is not intended to be interpreted in a limiting manner, such as necessarily specifying the location, inclusion, and/or relative arrangement of the components described herein. For example, a data acquisition component 122 as illustrated in FIG. 1 may be part of a rotor 104 portion of the examination apparatus, or more particularly may be part of a detector array 106, for example.

In the example environment 100, an object examination apparatus 108 is configured to examine one or more objects 102 (e.g., a series of suitcases at an airport, a human patient, etc.). The object examination apparatus 108 can comprise a rotor 104 and a stator 110. During an examination of the object(s) 102, the object(s) 102 can be placed on a support article 112, such as a bed or conveyor belt, and selectively positioned in an examination region 114 (e.g., a hollow bore in the rotor 104) by the support article 112. While the object(s) 102 are in the examination region 114, the rotor 104 can be rotated about the object(s) 102 by a rotator 116 (e.g., motor, drive shaft, chain, etc.).

The rotor 104 may surround a portion of the examination region 114 and may comprise one or more radiation sources 118 (e.g., an ionizing x-ray source, gamma source, etc.) and a detector array 106 that is mounted on a substantially diametrically opposite side of the rotor 104 relative to the radiation source(s) 118.

During an examination of the object(s) 102, the radiation source(s) 118 emits fan, cone, wedge, and/or other shaped radiation 120 configurations into the examination region 114 of the object examination apparatus 108. It will be appreciated to those skilled in the art that such radiation may be emitted substantially continuously and/or may be emitted intermittently (e.g., a short pulse of radiation 120 is emitted followed by a resting period during which the radiation source(s) 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of radiation photons that are detected by the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 is configured to directly convert (e.g., using amorphous selenium and/or other direct conversion materials) and/or indirectly convert (e.g., using photodetectors and/or other indirect conversion materials) detected radiation into signals that can be transmitted from the detector array 106 to a data acquisition component 122 configured to compile signals that were transmitted within a predetermined time interval, or measurement interval, using techniques known to those skilled in the art (e.g., binning, integration, etc.). It will be appreciated that such a measurement interval may be referred to by those skilled in the art as a "view" and generally reflects signals generated from radiation 120 that was emitted while the radiation source 118 was at a particular angular range relative to the object 102. Based upon the compiled signals, the data acquisition component 122 can generate projection data indicative of the compiled signals, for example.

The example environment 100 further comprises an image reconstructor 124 configured to receive the projection data that is output by the data acquisition component 122. The image reconstructor 124 is configured to generate image data from the projection data using a suitable analytical, iterative, and/or other reconstruction technique (e.g., back-projection reconstruction, tomosynthesis reconstruction, iterative reconstruction, etc.). In this way, the data is converted from projection space to image space, a domain that may be more understandable by a user 130 viewing the image(s), for example.

The example environment 100 also includes a terminal 126, or workstation (e.g., a computer), configured to receive the image(s), which can be displayed on a monitor 128 to the user 130 (e.g., security personnel, medical personnel, etc.). In this way, a user 130 can inspect the image(s) to identify areas of interest within the object(s) 102. The terminal 126 can also be configured to receive user input which can direct operations of the object examination apparatus 108 (e.g., a speed to rotate, a speed of a conveyor belt, etc.).

In the example environment 100, a controller 132 is operably coupled to the terminal 126. In one example, the controller 132 is configured to receive user input from the terminal 126 and generate instructions for the object examination apparatus 108 indicative of operations to be performed. For example, the user 130 may want to reexamine the object(s) 102, and the controller 132 may issue a command instructing the support article 112 to reverse direction (e.g., bringing the object(s) 102 back into an examination region 114 of the object examination apparatus 102).

Figure 2:
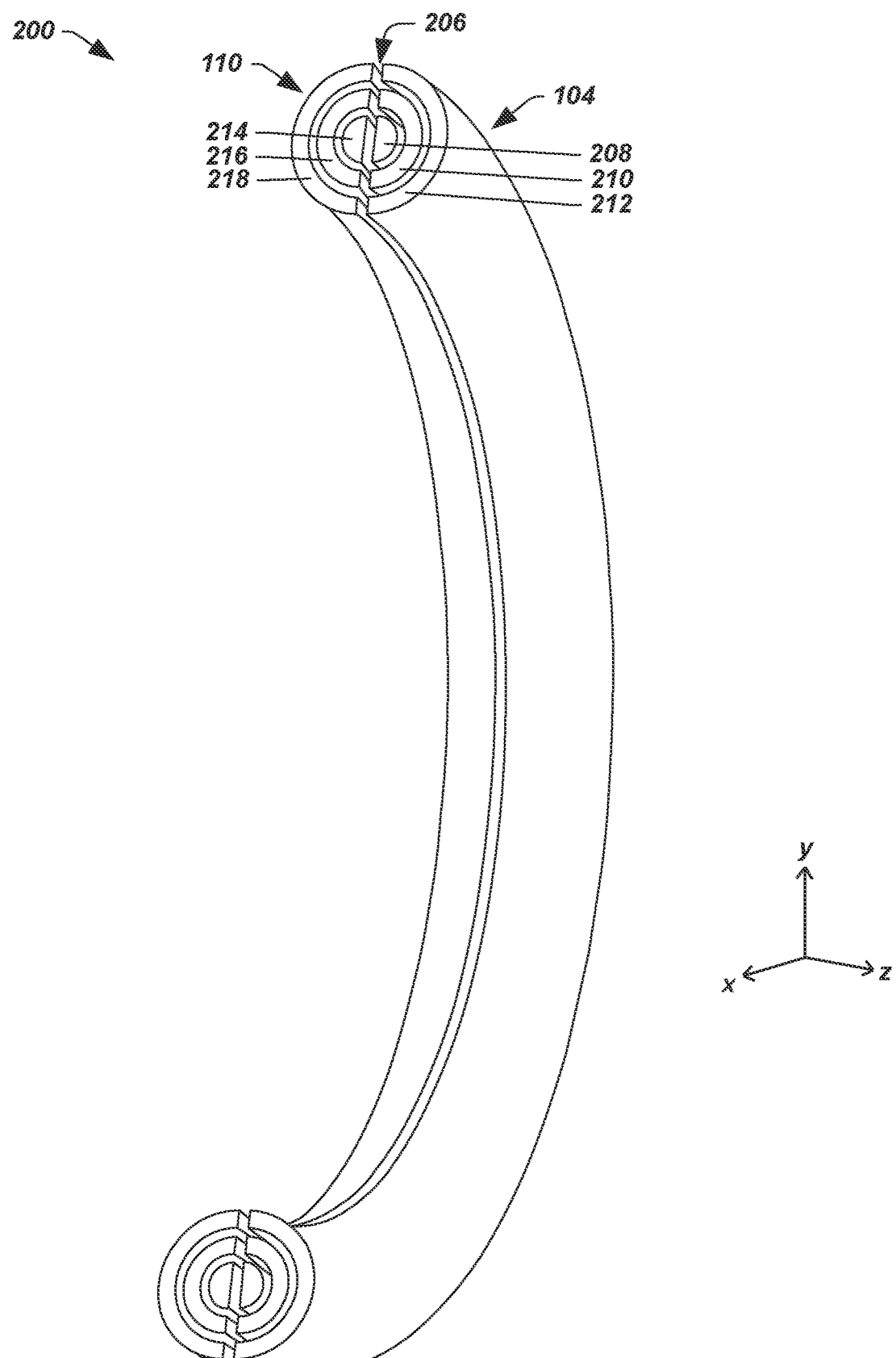
FIG. 2 illustrates an example power coupling device.

FIG. 2 illustrates a high-level, cross-sectional view (e.g., taken along line 2-2 in FIG. 1) of an example power coupling device 200 comprising the rotor 104 and the stator 110. As illustrated herein, the rotor 104 and the stator 110 are respectively half circles separated from one another via a planar airgap 206, and as will be described below, power is configured to be transferred between the stator 110 to the rotor 104. In this way, in an example, power may be supplied to electrical components comprised within the rotor or the stator, such as a radiation source (e.g., 118 in FIG. 1) and/or detector array (e.g., 106 in FIG. 1) without using slip-rings and/or brushes, for example.

In an example, the rotor 104 and the stator 110 respectively may comprise three coaxial half-shells or layers. For example, the rotor 104 comprises, being in order from the airgap 206, a winding 208, a core 210, and a shell 212, and the stator 110 comprises, being in order from the airgap 206, a winding 214, a core 216, and a support structure 218. It will be appreciated that between the respective layers, there may be gaps of indeterminate thickness (e.g., intended to include the possibility of zero gap).

Figure 3:
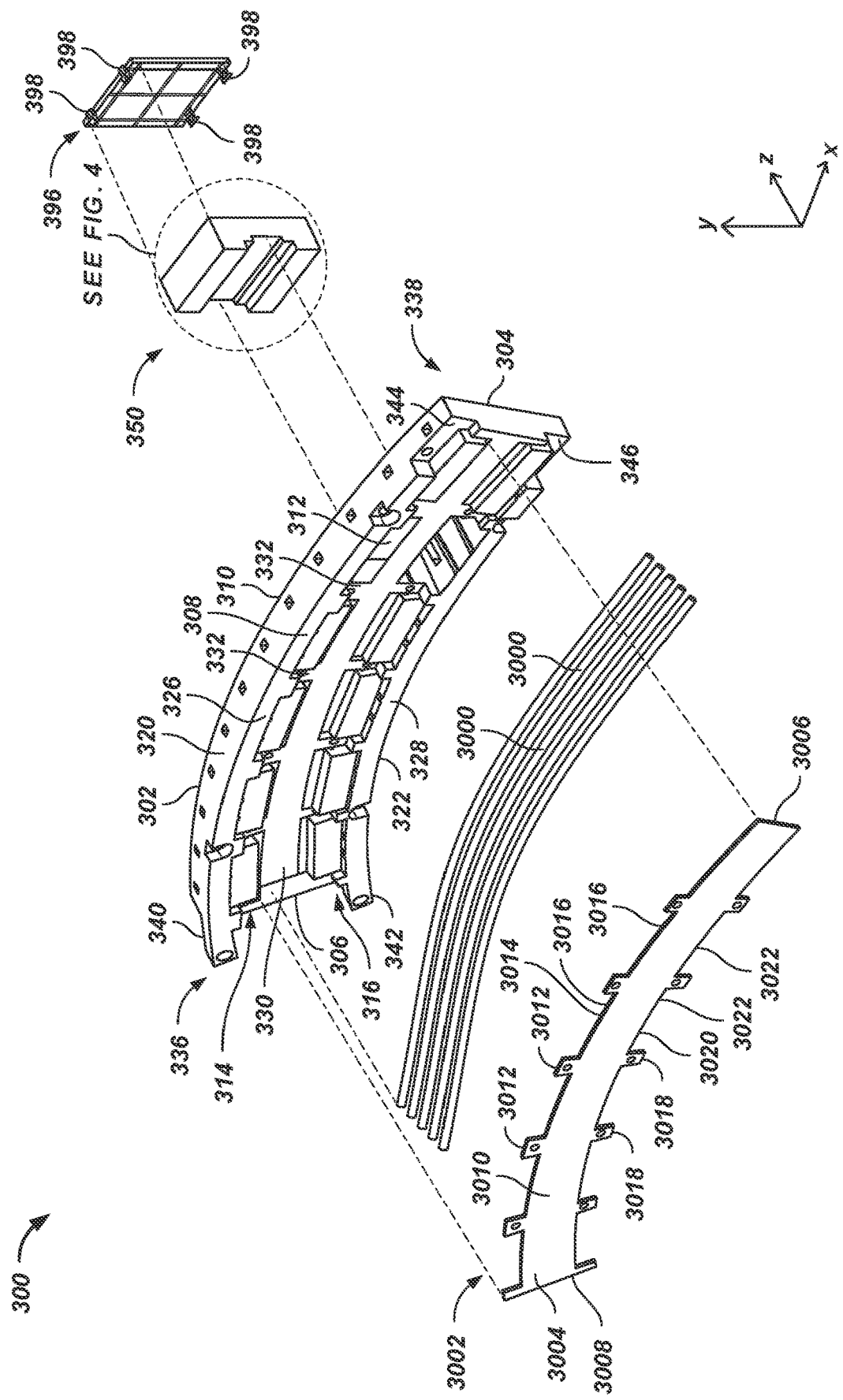
FIG. 3 illustrates an example segment for a power coupling device.

Referring now to FIG. 3, the rotor 104 and/or the stator 110 may be segmented into a plurality of interlocking segments, which may be assembled to form the ring-shape shown in FIG. 2. FIG. 3 illustrates an enlarged, exploded view of an example segment 300. While only one segment 300 is illustrated in FIG. 3, it will be appreciated that rotor 104 and/or the stator 110 may comprise a plurality of similarly configured segments.

The segment 300 comprises a support structure 302 (e.g., shell 212 in FIG. 2). The support structure 302 can extend non-linearly (e.g., along a non-linear axis) between a first support end 304 and a second support end 306. The support structure 302 may comprise any number of materials. In a possible example, the support structure 302 may comprise metal or non-metal materials and may be electrically conductive or non-conductive. For example, the support structure 302 may comprise a plastic material, such as a plastic material that is formed via an injection molding process.

Figure 10:
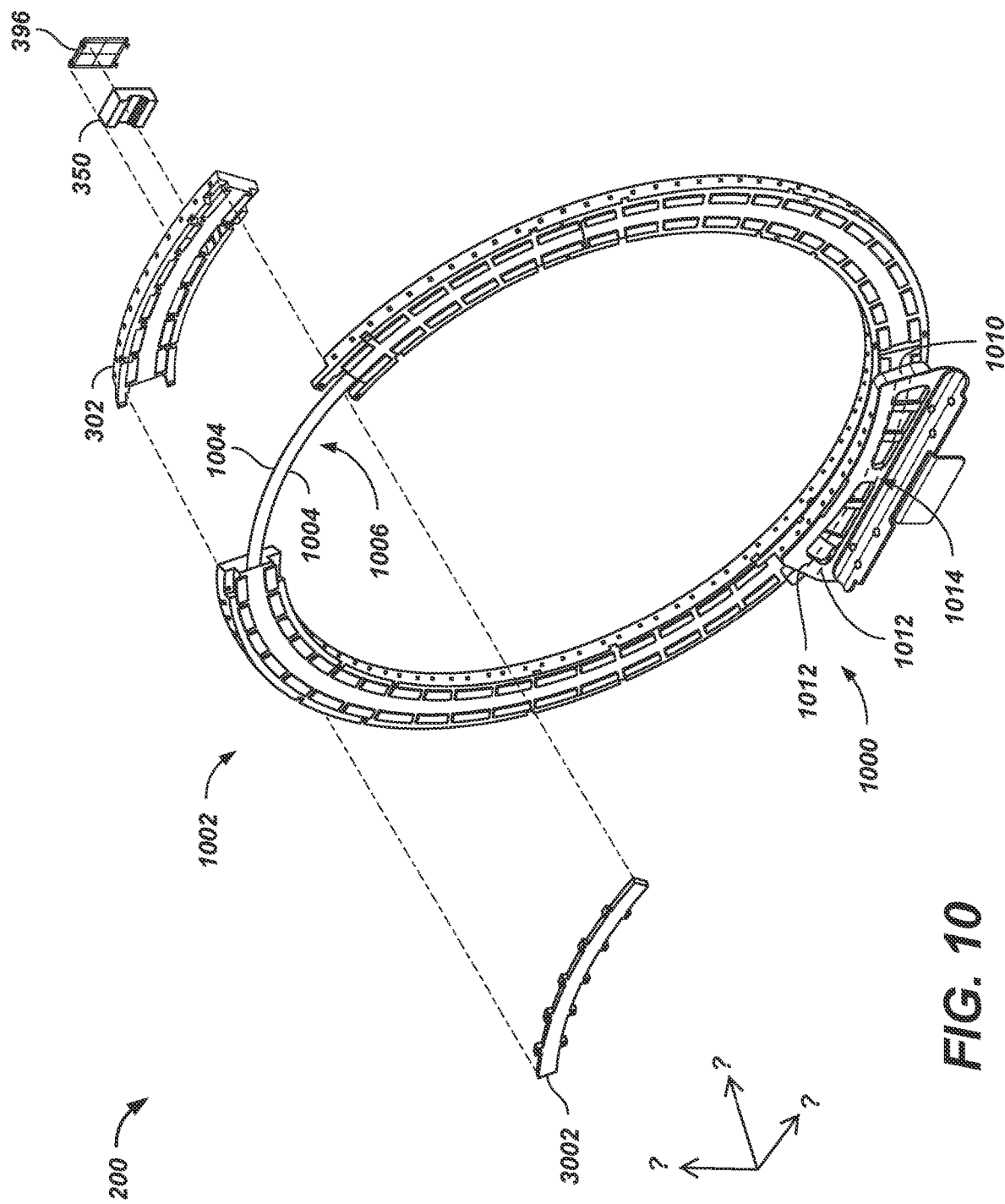
FIG. 10 illustrates example segments arranged to form a first winding and a second winding of a transformer.

The support structure 302 can define one or more openings 312 extending between a first support side 308 and a second support side 310. In an example, the openings 312 of the support structure 302 can be arranged as a first row of openings 314 and a second row of openings 316. The first row of openings 314 can be spaced apart from each other so as to be arranged to extend non-linearly between the first support end 304 and the second support end 306. In such an example, the first row of openings 314 can define openings through the support structure 302 between the first support side 308 and the second support side 310. The openings 312 of the first row of openings 314 are illustrated as having a substantially rectangular shape, though any number of shapes (e.g., quadrilateral, square, rounded, oval, etc.) are envisioned. In an example, as is illustrated in FIG. 10, the first row of openings 314 can be spaced apart from each other so as to be arranged to extend circularly about an axis.

The second row of openings 316 can be spaced apart from each other so as to be arranged to extend non-linearly between the first support end 304 and the second support end 306. For example, in some embodiments, the second row of openings 316 and the first row of openings 314 each form an arc-shaped structure, where the arc-shaped structure formed by the second row of openings 316 and the arc-shaped structure formed by the first row of openings 314 are substantially coaxial. Moreover, while the openings 312 of the second row of openings 316 are illustrated as having a substantially rectangular shape, any number of shapes (e.g., quadrilateral, square, rounded, oval, etc.) are envisioned. In an example, as is illustrated in FIG. 10, the second row of openings 316 can be spaced apart from each other so as to be arranged to extend circularly about an axis.

In an example, the first row of openings 314 can extend substantially parallel to the second row of openings 316. For example, the first row of openings 314 can be positioned in closer proximity to an outer side 320 of the support structure 302. The second row of openings 316 can be positioned in closer proximity to an inner side 322 of the support structure 302. As such, the first row of openings 314 may be spaced apart from the second row of openings 316, with the space having a substantially constant distance between the first support end 304 and the second support end 306.

In the illustrated example, the support structure 302 can extend partially about a central axis, such that the support structure 302 comprises a portion of a ring or circle. As such, in an example, the outer side 320 may define an outer radial side of the support structure 302. In an example, the inner side 322 may define an inner radial side of the support structure 302. In this way, the inner side 322 may be located in closer proximity to the central axis than the outer side 320. Likewise, in an example, the second row of openings 316 may be located in closer proximity to the central axis than the first row of openings 314.

The support structure 302 may comprise an outer support wall 326 that extends along the outer side 320. The support structure 302 may comprise an inner support wall 328 that extends along the inner side 322. The outer support wall 326 can extend substantially parallel to the inner support wall 328. In an example, the outer support wall 326 and the inner support wall 328 extend non-linearly between the first support end 304 and the second support end 306. The outer support wall 326 can be located at an outer radial side of the first row of openings 314. The inner support wall 328 can be located at an inner radial side of the second row of openings 316.

The support structure 302 comprises a support member 330 that extends non-linearly between the first support end 304 and the second support end 306. The support member 330 can extend substantially parallel to the outer support wall 326 and/or to the inner support wall 328. In an example, the support member 330 may be disposed between the outer support wall 326 and the inner support wall 328. For example, the outer support wall 326 may be located on a first side of and spaced apart from the support member 330. The inner support wall 328 may be located on a second side of and spaced apart from the support member 330. In an example, the support member 330 may be spaced a substantially equal distance from the outer support wall 326 and the inner support wall 328. In an example, the first row of openings 314 may be defined between the support member 330 and the outer support wall 326. In an example, the second row of openings 316 may be defined between the support member 330 and the inner support wall 328.

The support structure 302 comprises one or more intermediate support walls 332. In an example, the intermediate support walls 332 can extend between the outer support wall 326 and the inner support wall 328. In such an example, the intermediate support walls 332 may extend substantially perpendicular to the outer support wall 326, the inner support wall 328, and/or the support member 330. The intermediate support walls 332 can extend substantially linearly between the inner support wall 328 at one end, and the outer support wall 326 at an opposing end.

The outer support wall 326, the inner support wall 328, the support member 330, and the intermediate support walls 332 can define at least some of the openings 312. For example, the outer support wall 326, the support member 330, and the intermediate support walls 332 can define the first row of openings 314. The inner support wall 328, the support member 330, and the intermediate support walls 332 can define the second row of openings 316.

In an example, the support structure 302 can be removably or non-removably attached to an adjacent support structure of an adjacent segment. For example, the support structure 302 may comprise a first attachment portion 336 and a second attachment portion 338. The first attachment portion 336 comprises an outer attachment extension 340 and an inner attachment extension 342. The outer attachment extension 340 projects from an end of the outer support wall 326 while the inner attachment extension 342 projects from an end of the inner support wall 328. In an example, the outer attachment extension 340 extends substantially parallel to the inner attachment extension 342. The outer attachment extension 340 and the inner attachment extension 342 may be radially spaced apart to define a gap, a space, an opening, etc. therebetween. In an example, the outer attachment extension 340 and the inner attachment extension 342 may define openings through which a fastener is configured to be received.

The second attachment portion 338 may comprise an outer attachment channel 344 and an inner attachment channel 346. The outer attachment channel 344 may be defined at an end of the outer support wall 326 opposite the outer attachment extension 340. The inner attachment channel 346 may be defined at an end of the inner support wall 328 opposite the inner attachment extension 342. The outer attachment channel 344 and the inner attachment channel 346 define a recess, an opening, etc. formed within the outer support wall 326 and the inner support wall 328. In an example, a length of the outer attachment channel 344 may be substantially similar to a length of the outer attachment extension 340. In an example, a length of the inner attachment channel 346 may be substantially similar to a length of the inner attachment extension 342. In some examples, an opening can be defined in the outer support wall 326 and the inner support wall 328 adjacent to the outer attachment channel 344 and the inner attachment channel 346 so as to receive a fastener, or the like.

In an example, the outer attachment extension 340 is configured to be received within an outer attachment channel of an adjacent support structure. Likewise, the inner attachment extension 342 is configured to be received within an inner attachment channel of the adjacent support structure. In such an example, the outer attachment extension 340 and the inner attachment extension 342 can receive fasteners through the openings for attaching the support structure 302 to the adjacent support structure.

The segment 300 comprises a core element 350. It will be appreciated that FIG. 3 illustrates a plurality of the core elements attached to the support structure 302. One core element 350 is not attached to and spaced apart from the support structure 302 for illustrative purposes. In operation, however, the core element 350 may be attached to the support structure 302.

Figure 4:
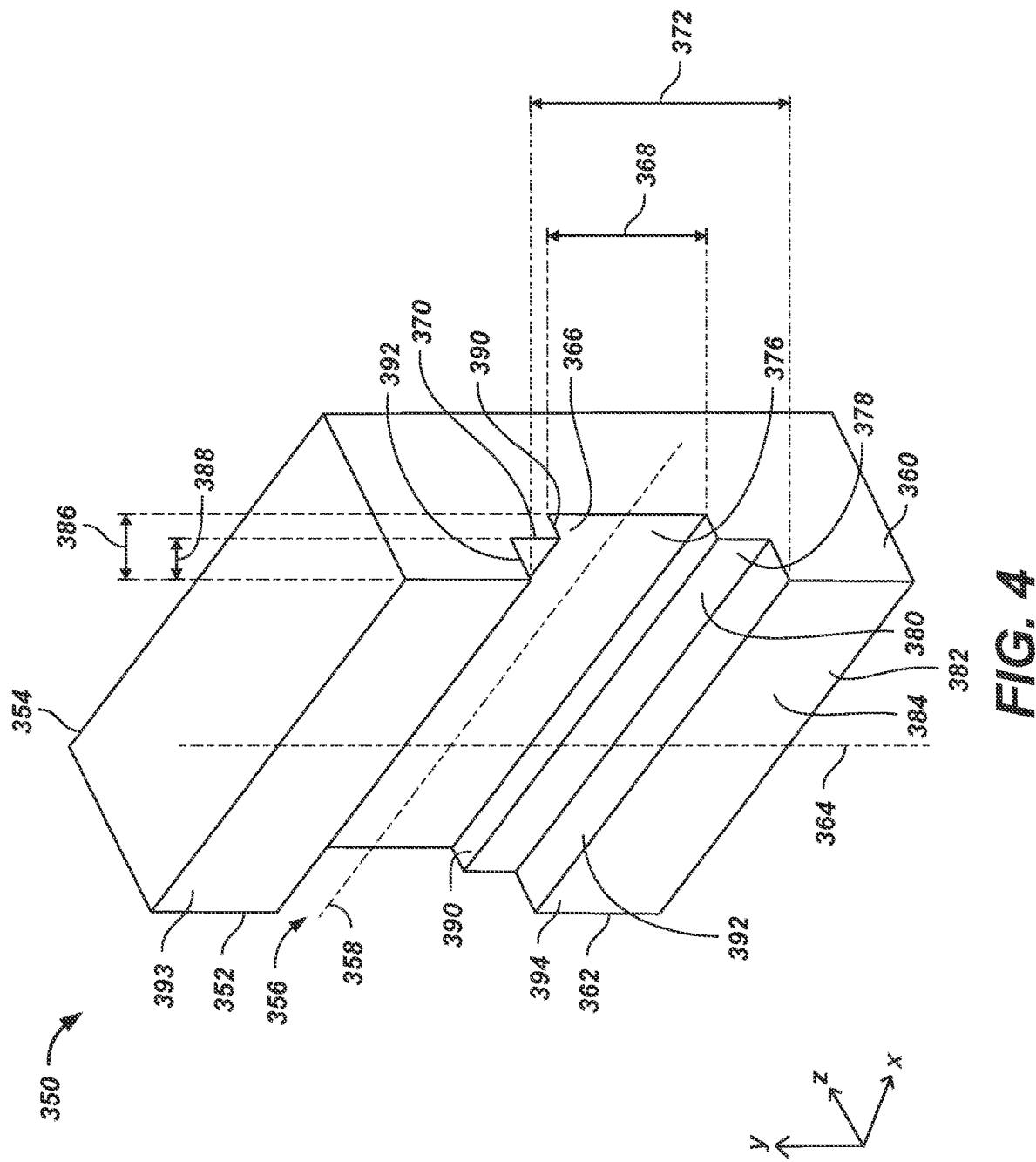
FIG. 4 illustrates an example core element for a segment.

With reference to FIGS. 3 and 4, the core element 350 may comprise any number of materials, such as a ferrite material. The core element 350 may be configured to be received within one or more of the openings 312 of the support structure 302. In an example, the core element 350 defines a first side 352 and a second side 354. The first side 352 of the core element 350 may face the support structure 302 while the second side 354 of the core element 350 may face away from the support structure 302.

The core element 350 can define a core channel 356 along the first side 352. In an example, the core channel 356 can extend along a first axis 358 between a first end 360 and a second end 362 of the core element 350. The core channel 356 defines an opening, a groove, a furrow, or the like formed along the first side 352 of the core element 350.

In an example, the core channel 356 can have a non-constant cross-sectional size from the first side 352 towards the second side 354 as measured along a second axis 364 that is substantially perpendicular to the first axis 358. For example, the core channel 356 can have a first channel portion 366 that has a first channel width 368 measured along the second axis 364. In such an example, the first channel width 368 may be large enough such that the first channel portion 366 can receive the support member 330.

The core channel 356 can have a second channel portion 370 that has a second channel width 372 measured along the second axis 364. In an example, the first channel width 368 may be different than the second channel width 372. For example, the first channel width 368 may be less than the second channel width 372. In this way, the cross-sectional size of the core channel 356 can decrease from the first side 352 towards the second side 354. Indeed, the second channel portion 370 has a larger cross-sectional size (e.g., the second channel width 372) than a cross-sectional size of the first channel portion 366 (e.g., the first channel width 368).

The core channel 356 can be at least partially defined by a back face 376 and an intermediate face 378. The intermediate face 378 can extend substantially parallel to the back face 376. In an example, the intermediate face 378 can define an intermediate plane 380. The first side 352 of the core element 350 can be defined by a front face 382 that defines a plane 384. In an example, the front face 382 extends substantially parallel to the intermediate face 378 and/or the back face 376.

The back face 376 of the core element 350 may extend substantially parallel to the plane 384, and may be spaced a first distance 386 from the plane 384. The intermediate face 378 may be spaced a second distance 388 from the plane 384. In the illustrated example, the first distance 386 may be different than the second distance 388. For example, the first distance 386 may be greater than the second distance 388. As such, the back face 376 may be located a greater distance from the front face 382 than the intermediate face 378.

In an example, the back face 376 may be bounded on opposing sides (e.g., upper side and lower side) by back walls 390. The back walls 390, which extend between the back face 376 and the intermediate face 378, may be substantially parallel to each other. The back walls 390 may be separated by the first channel width 368. In an example, the back walls 390 may be substantially perpendicular to the back face 376 and/or to the intermediate face 378.

The intermediate face 378 may be bounded on opposing sides (e.g., upper side and lower sides) by intermediate walls 392. The intermediate walls 392, which extend between the intermediate face 378 and the front face 382, may be substantially parallel to each other. The intermediate walls 392 may be separated by the second channel width 372. In an example, the intermediate walls 392 may be substantially perpendicular to the back face 376 and/or to the intermediate face 378 and/or to the front face 382.

The core element 350 can therefore define a first extension portion 393 and a second extension portion 394. In an example, the first extension portion 393 and the second extension portion 394 can have a substantially matching length between the first side 352 and the second side 354. In an example, this length may be greater than a length of the core element 350 (e.g., between the first side 352 and the second side 354) as measured at a central location between the first extension portion 393 and the second extension portion 394. In the illustrated example, the core element 350 can be substantially U-shaped, though, other possible shapes are envisioned.

With continuing reference to FIG. 3, the segment 300 comprises an attachment structure 396. The attachment structure 396 can be removably attached to the support structure 302. In an example, the attachment structure 396 is configured to attach the core element 350 to the support structure 302. For example, the attachment structure 396 can be positioned to face the second side 354 of the core element 350. The attachment structure 396 can be moved into contact with the support structure 302 and the second side 354 of the core element 350.

The attachment structure 396 comprises one or more attachment portions 398 that facilitate attachment of the attachment structure 396 to the support structure 302. In a possible example, the attachment portions 398 comprise openings into which fasteners can be received. The fasteners can pass through the attachment portions 398 and into openings in the second support side 310 of the support structure 302, so as to attach the attachment structure 396 to the support structure 302. In other examples, the attachment portions 398 may comprise locking structures such as locking clips, locking tabs, or the like that can removably engage and lock with the support structure 302. In the aforementioned examples, the attachment portions 398 can allow for removable attachment of the attachment structure 396 to the support structure 302.

The core element 350 can be sandwiched between the attachment structure 396 and the support member 330 of the support structure 302. In this way, the attachment structure 396 can be attached to the support structure 302, such as with the attachment portions 398. As such, the core element 350 can be held in place and in a substantially fixed position with respect to the support structure 302 when the attachment structure 396 is attached to the support structure 302. In an example, the attachment structure 396 can be selectively detached from the support structure 302, thus allowing for detachment and removal of the core element 350 from the support structure 302.

The segment 300 comprises one or more inductive elements 3000. The inductive elements 3000 are comprised of coils comprising electrically conductive wires (e.g., copper wire) or the like. In this way, electric current can pass through the inductive elements 3000. In an example, the inductive elements 3000 may face the first side 352 of the core element 350. The inductive elements 3000 are configured to be received within the core channel 356 of the core element 350. For example, the inductive elements 3000 may be received within the second channel portion 370 of the core channel 356. As such, the inductive elements 3000 can border and/or be positioned adjacent to the support member 330 of the support structure 302. In this way, the support member 330 can be received within the first channel portion 366 of the core channel 356 while the inductive elements 3000 may be received within the second channel portion 370.

The segment 300 comprises a front attachment structure 3002 that may be removably attached to the support structure 302 diametrically opposed to the attachment structure 396. The front attachment structure 3002 comprises an attachment body 3004 that extends between a first end 3006 and a second end 3008. The front attachment structure 3002 can have a length that is substantially similar to the length of the support structure 302. In some examples, the front attachment structure 3002 can extend non-linearly between the first end 3006 and the second end 3008. As such, the front attachment structure 3002 can extend along an arc that substantially matches an arc along which the support structure 302 extends.

The attachment body 3004 comprises a central attachment portion 3010. The central attachment portion 3010 extends non-linearly between the first end 3006 and the second end 3008 along the arc. In an example, when the front attachment structure 3002 is attached to the support structure 302, the central attachment portion 3010 can be positioned adjacent to the inductive elements 3000. The central attachment portion 3010 can extend substantially parallel to the support member 330, with the inductive elements 3000 positioned between the support member 330 on one side and the central attachment portion 3010 on an opposing side. In some examples, the central attachment portion 3010 can be received within the second channel portion 370 of the core channel 356.

The attachment body 3004 comprises one or more outer attachment portions 3012. The outer attachment portions 3012 project and/or extend from the central attachment portion 3010. In an example, the outer attachment portions 3012 may be located on an outer side 3014 of the central attachment portion 3010. The outer attachment portions 3012 may be spaced apart to define outer spaces 3016 between neighboring outer attachment portions 3012. In an example, the outer attachment portions 3012 can extend substantially parallel to the intermediate support walls 332 of the support structure 302. In this example, a size of the outer spaces 3016 can substantially match a size of the first row of openings 314. As such, the outer spaces 3016 can be aligned with the first row of openings 314 while the outer attachment portions 3012 can be aligned with the intermediate support walls 332.

The attachment body 3004 comprises one or more inner attachment portions 3018. The inner attachment portions 3018 project and/or extend from the central attachment portion 3010. In an example, the inner attachment portions 3018 may be located on an inner side 3020 of the central attachment portion 3010. As such, the inner attachment portions 3018 may be positioned on an opposite side of the central attachment portion 3010 from the outer attachment portions 3012. The inner attachment portions 3018 may be spaced apart to define inner spaces 3022 between neighboring inner attachment portions 3018. In an example, the inner attachment portions 3018 can extend substantially parallel to the intermediate support walls 332 of the support structure 302. In this example, a size of the inner spaces 3022 can substantially match a size of the first row of openings 314. As such, the outer spaces 3016 can be aligned with the second row of openings 316 while the inner attachment portions 3018 can be aligned with the intermediate support walls 332.

The outer attachment portions 3012 and the inner attachment portions 3018 can facilitate attachment of the front attachment structure 3002 to the support structure 302. In an example, the outer attachment portions 3012 and the inner attachment portions 3018 comprise openings into which fasteners can be received. The fasteners can pass through the outer attachment portions 3012 and the inner attachment portions 3018 and into openings in one or more of the outer support wall 326, inner support wall 328, support member 330, or intermediate support wall 332 of the support structure 302. As such, the fasteners can function to attach the front attachment structure 3002 to the first support side 308 of the support structure 302. In other examples, the outer attachment portions 3012 and the inner attachment portions 3018 may comprise structures such as locking clips, locking tabs, or the like that can removably engage and lock with the support structure 302. In the aforementioned examples, the fasteners that pass through the outer attachment portions 3012 and the inner attachment portions 3018 can allow for removable attachment of the front attachment structure 3002 to the support structure 302.

Figure 5:
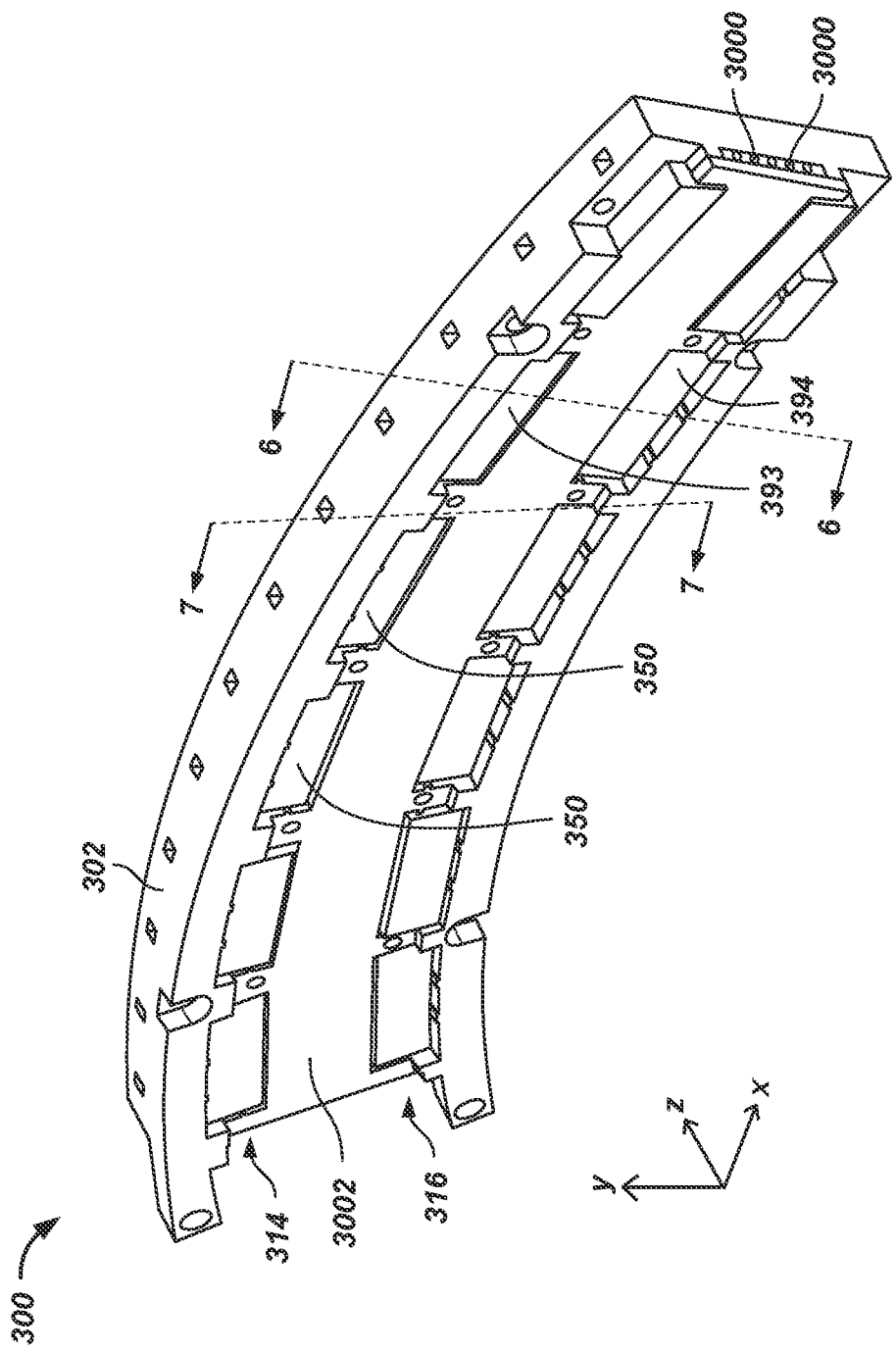
FIG. 5 illustrates an example segment for a power coupling device.

Turning to FIG. 5, an example of the assembled segment 300 is illustrated. In this example, the core elements 350 can be at least partially received within the first row of openings 314 and the second row of openings 316 of the support structure 302. For example, a portion of the first extension portion 393 of the core elements 350 can be received within the first row of openings 314. In an example, a portion of the second extension portion 394 of the core elements 350 can be received within the second row of openings 316.

With the core element 350 received within the openings 314, 316, the attachment structure 396 (e.g., illustrated in FIG. 3) can be attached to the second support side 310 of the support structure 302. By attaching the attachment structure 396 to the support structure 302, the core element 350 can be held in a substantially fixed position with respect to the support structure 302. The core element 350 may be substantially limited from being inadvertently removed from the support structure 302.

In an example, the front attachment structure 3002 can be attached to the first support side 308 of the support structure 302. The front attachment structure 3002 can hold the inductive elements 3000 in place with respect to the support structure 302 and the core element 350 in a substantially fixed position. As such, the inductive elements 3000 may be substantially limited from being inadvertently removed from the core channel 356 of the core element 350.

Figure 6:
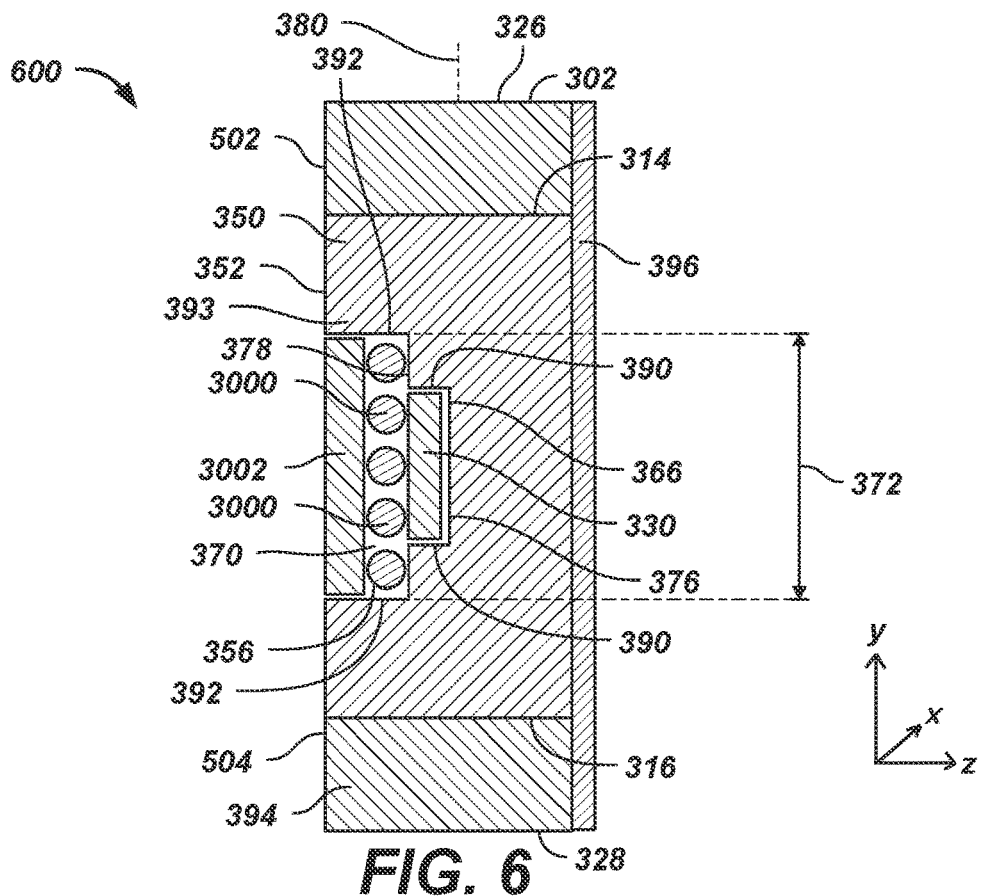
FIG. 6 illustrates a cross-section of a segment for a power coupling device illustrating a core element.

FIG. 6 illustrates a cross-sectional view 600 (e.g., taken along line 6-6 in FIG. 5) of the segment 300. In the illustrated example, the core element 350 can be disposed between the support structure 302 and the attachment structure 396. For example, the support member 330 of the support structure 302 may be received within the first channel portion 366 of the core channel 356 of the core element 350. The support member 330 can be disposed between the back walls 390 and adjacent to the back face 376 of the core element 350. In some examples, when the support member 330 is received within the first channel portion 366, a face of the support member 330 and the intermediate face 378 may be substantially planar (e.g., such as by both extending along the intermediate plane 380). As such, a central portion of the core element 350 may be disposed between the support member 330 of the support structure 302 and the attachment structure 396.

The inductive elements 3000 can be received within the second channel portion 370 of the core channel 356. In an example, the inductive elements 3000 may be spaced apart and positioned to extend adjacent to and/or in contact with the support member 330 of the support structure 302. The inductive elements 3000 can be positioned between the intermediate walls 392. In the illustrated example, the inductive elements 3000 may be spaced apart from the intermediate walls 392. In some examples, the inductive elements 3000 may be disposed on a first side of the intermediate plane 380 while the support member 330 of the support structure 302 may be disposed at least partially on a second side of the intermediate plane 380. The support member 330 of the support structure 302 may therefore be disposed between the core element 350 (e.g., a central portion of the core element defined, in part, by the back face 376) and the inductive elements 3000.

In an example, the front attachment structure 3002 can be disposed at least partially within the second channel portion 370 of the core channel 356 between the intermediate walls 392. In an example, the length of the front attachment structure 3002 (e.g., as measured up/down in FIG. 6) may be less than the second channel width 372 of the second channel portion 370. As such, the front attachment structure 3002 can be selectively inserted into the second channel portion 370 and removed from the second channel portion 370. In an example, a face of the front attachment structure 3002 and the front face 382 may be substantially planar (e.g., such as by both extending along the plane 384). In this example, inductive elements 3000 may be disposed between the front attachment structure 3002 and the inner support member 330 of the support structure 302.

The core elements 350 can be received within the first row of openings 314 and the second row of openings 316. For example, the first extension portion 393 may be received within the first row of openings 314. In the illustrated example, the front face 382 of the first extension portion 393 may be substantially planar to a front support face 502 defined along the outer support wall 326. The second extension portion 394 may be received within the second row of openings 316. In the illustrated example, the front face 382 of the second extension portion 394 may be substantially planar to a front support face 504 defined along the inner support wall 328. As such, in an example, front faces of the outer support wall 326, the first extension portion 393, the front attachment structure 3002, the second extension portion 394, and the inner support wall 328 may be substantially planar.

Figure 7:
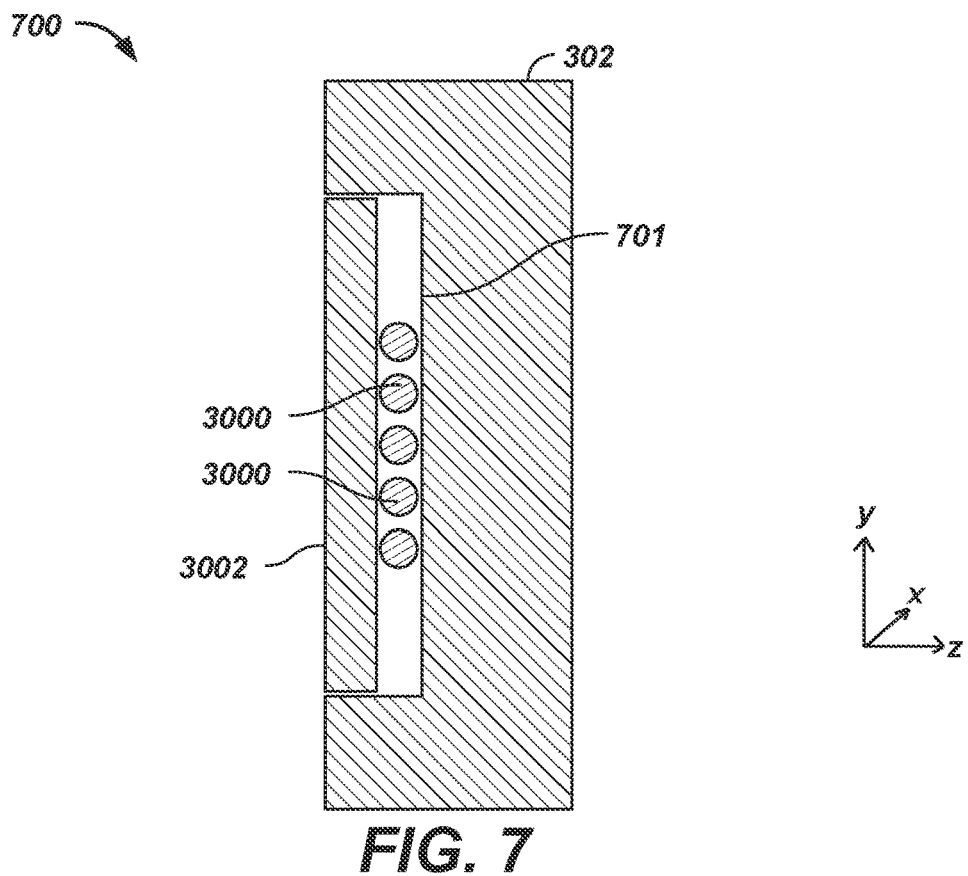
FIG. 7 illustrates a cross-section of a segment for a power coupling device illustrating a location between neighboring core elements.

FIG. 7 illustrates a cross-sectional view 700 (e.g., taken along line 7-7 in FIG. 5) of the segment 300. In the illustrated example, the cross-sectional view 700 is taken between neighboring core elements 350. The front attachment structure 3002 can assist in maintaining the inductive elements 3000 in a fixed position relative to the support structure 302. For example, the inductive elements 3000 can be positioned between the front attachment structure 3002 and the support structure 302.

In an example, the inductive elements 3000 may extend adjacent to a central support face 701 of the support structure 302. The central support face 701 may be substantially planar and extend between an outer side (e.g., upper side) and an inner side (e.g., lower side) of the support structure 302. The central support face 701 can extend substantially parallel to the front attachment structure 3002, with the front attachment structure 3002 spaced apart from the central support face 701 to define an opening therebetween. The inductive elements 3000 may be received within the opening so as to be maintained in place between the front attachment structure 3002 and the central support face 701.

In the illustrated example, the inductive elements 3000 may be substantially supported along a length of the support structure 302 between the first support end 304 and the second support end 306. For example, at locations between neighboring core elements 350 (e.g., as illustrated in FIG. 7), the inductive elements 3000 may be held in place between the front attachment structure 3002 and the central support face 701 of the support structure 302. When the inductive elements 3000 are received within the core channel 356 of the core element 350 (e.g., as illustrated in FIG. 6), the inductive elements 3000 may be held in place between the front attachment structure 3002 and the support member 330 of the support structure 302. In this way, the inductive elements 3000 may be held in place and substantially limited from becoming inadvertently removed from the core channel 356 of the core element 350.

Figure 8:
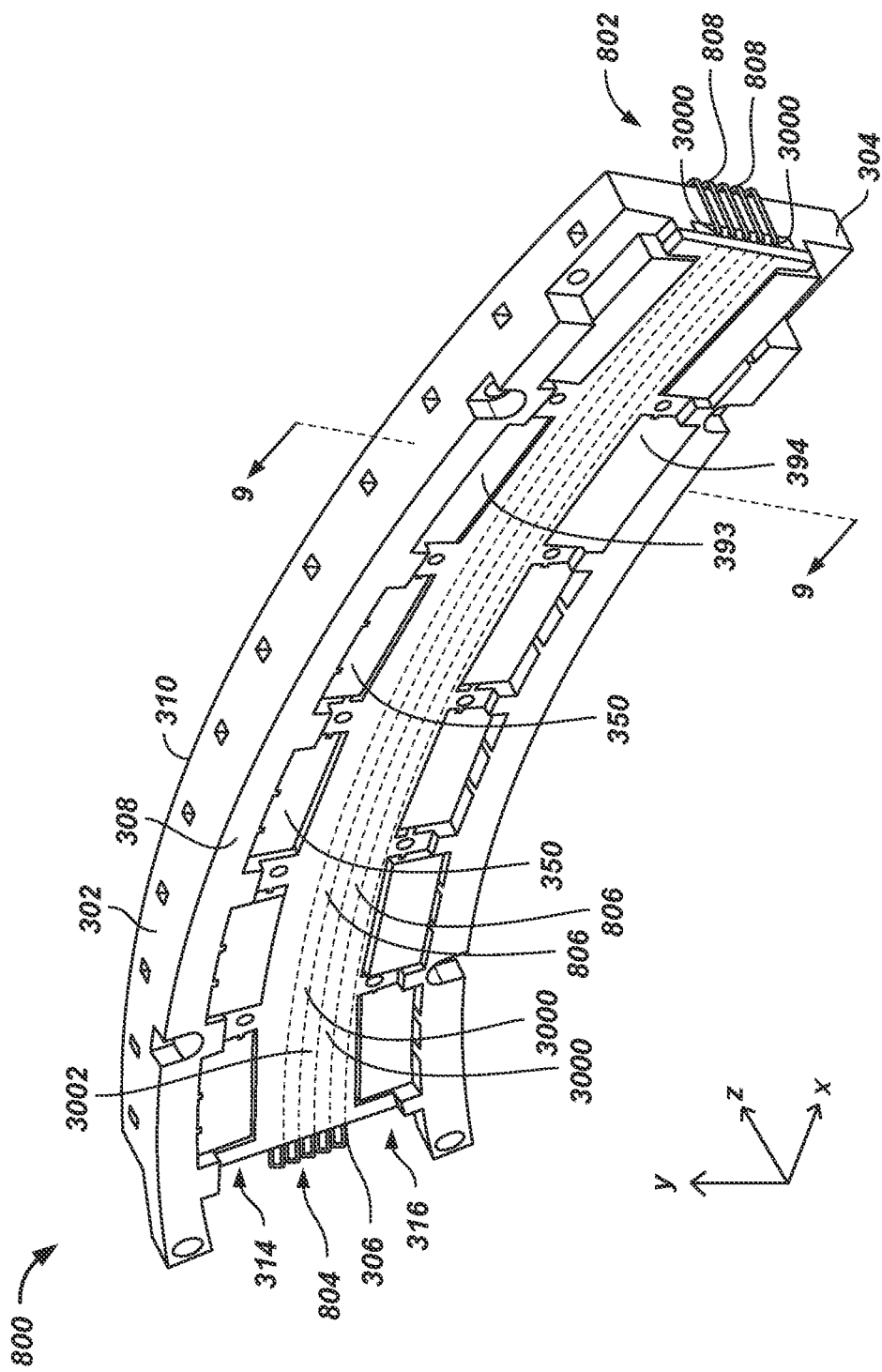
FIG. 8 illustrates a second example segment for a power coupling device.

Turning to FIG. 8, a second example segment 800 is illustrated. As with the previous examples, the inductive elements 3000 may be at least partially received within the core channels 356 of the core elements 350. It will be appreciated that the inductive elements 3000 are illustrated at least partially with dashed lines because the inductive elements 3000 are obstructed from view by the front attachment structure 3002.

The inductive elements 3000 can be wound around the core element 350 from the first side 352 to the second side 354 (e.g., first side 352 and second side 354 illustrated in FIG. 4). For example, the inductive elements 3000 can exit the support structure 302 at the first support end 304 and the second support end 306. The inductive elements 3000 can be wound around the support structure 302 at a first winding location 802 and a second winding location 804. At the first winding location 802 and the second winding location 804, the inductive elements 3000 can be wound around the support structure 302 so as to extend along the second support side 310 of the support structure 302. The inductive elements 3000 can therefore define a substantially closed loop that extends along the first support side 308 and the second support side 310 of the support structure 302.

In this example, the inductive elements 3000 may comprise first inductive portions 806 and second inductive portions 808. The first inductive portions 806 may be received within the core channel 356 of the core element 350 while the second inductive portions 808 may not be received within the core channel 356. In still other embodiments, the support structure 302 may comprised a notched portion in which the second inductive portions 808 are received. Moreover, a cap may be disposed over the support structure 302 to at least partially cover the second inductive portions 808 while seated within the notched portion of the support structure 302.

Figure 9:
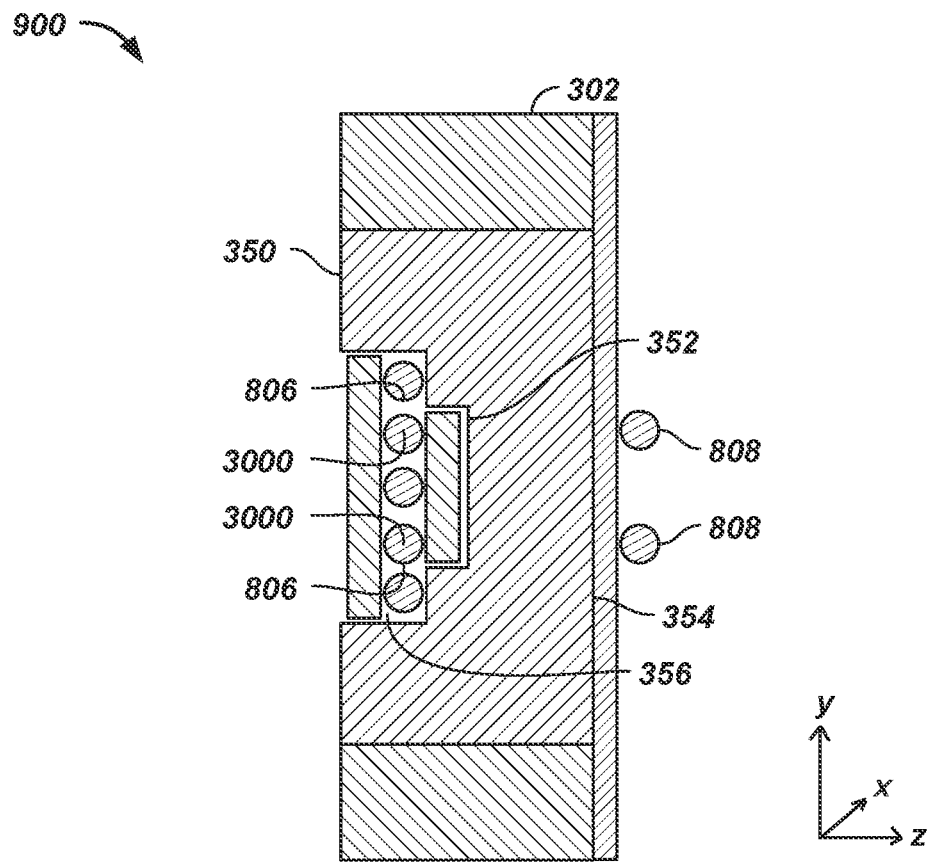
FIG. 9 illustrates a cross-section of a segment for a power coupling device illustrating a core element.

FIG. 9 illustrates a cross-sectional view 900 (e.g., taken along line 9-9 in FIG. 8) of the segment 800. In the illustrated example, a sectional view of the first inductive portion 806 and the second inductive portion 808 of the inductive elements 3000 is illustrated. The first inductive portion 806 may be received within the core channel 356, such that the first inductive portion 806 extends along the first side 352 of the core element 350. The second inductive portion 808 may not be received within the core channel 356. Rather, the second inductive portion 808 can extend along the second side 354 of the core element 350. As such, in this example, the core element 350 may be disposed between the first inductive portion 806 and the second inductive portion 808.

It will be appreciated that the second inductive portion 808 is not limited to extending along the second side 354 of the core element 350. Rather, the second inductive portion 808 may extend along a different side of the core element 350 while still not being received within the core channel 356. For example, the second inductive portion 808 may extend along an upper surface of the support structure 302, along a lower surface of the support structure 302, etc. In these examples, the first inductive portions 806 may be connected to the second inductive portion 808 such that the inductive elements 3000 define a substantially continuous loop.

Turning to FIG. 10, the power coupling device 200 is illustrated. In an example, the power coupling device 200 comprises a plurality of segments 1000 that are configured to transfer power between the stator 110 and the rotor 104. It will be appreciated that one of the plurality of segments 1000 is illustrated in a partially disassembled state for the purposes of illustration so as to show the relationship between portions of the segment. In operation, however, the plurality of segments 1000 may be in a fully assembled state.

In an example, the segments 1000 comprise a first subset 1002 of one or more segments, such as a plurality of segments having a configuration similar to the configuration illustrated in FIGS. 3-7 (e.g., where the inductive elements 3000 is nearly disposed on one side of the core element 350). The first subset 1002 of the plurality of segments 1000 can be arranged to define a ring. The segments 1000 may comprise the segment 300 (e.g., illustrated in FIG. 3), with the other segments substantially similar to the segment 300. For example, the segment 300, and the plurality of segments 1000, may comprise the support structure 302, the core element 350, the attachment structure 396, the front attachment structure 3002, etc.

The first subset 1002 may comprise first inductive elements 1004. In the illustrated example, the first inductive elements 1004 may be substantially similar to the inductive elements 3000 illustrated in FIG. 3. Any number of first inductive elements 1004 (e.g., one or more) are envisioned, though in the illustrated example of FIG. 10, the first inductive elements 1004 comprise two inductive elements. The first inductive elements 1004 may extend through the support structures of the plurality of segments 1000, such that the first inductive elements 1004 can be arranged to form a ring. The first inductive elements 1004 can be maintained in place with respect to the support structures and core elements of the segments 1000 in a similar manner as described with respect to FIGS. 3 to 7.

The first inductive elements 1004 of the first subset 1002 may be coupled in parallel to define a first winding 1006 of a transformer. In some examples, the first winding 1006 may comprise a primary winding, which generates a magnetic field in response to an input voltage, or a secondary winding, which has an output voltage induced as a result of the magnetic field generated by the primary winding.

The segments 1000 comprise a second subset 1010 of one or more segments, such as one or more segments having a configuration similar to the configuration illustrated in FIGS. 8 and 9 (e.g., where the inductive elements 3000 can be wound around the core element 350 from the first side 352 to the second side). The second subset 1010 of the plurality of segments 1000 can be arranged to define a partial ring. That is, in an example, the second subset 1010 of the plurality of segments 1000 can extend partially about a center axis (e.g., the z-axis) and may define a non-closed shape (e.g., less than a full ring). As such, the second subset 1010 can have a first end and an opposing second end, with the second subset 1010 extending about the center axis (e.g., the z-axis) between the first end and the second end. In an example, the second subset 1010 of the plurality of segments 1000 that defines a partial ring can form one of the stator 110 or the rotor 104.

It will be appreciated that in the example of FIG. 10, the second subset 1010 comprises a single segment. However, in other examples, the second subset 1010 is not so limited, and may comprise a plurality of segments arranged adjacent to each other so as to extend at least partially about the center axis (e.g., the z-axis). In some examples, the first subset 1002 and the second subset 1010 can extend about a common center axis (e.g., the z-axis), such that the first subset 1002 and the second subset 1010 may be substantially co-axial. In the illustrated example, the second subset 1010 can be located adjacent to and may extend substantially parallel to the first subset 1002. In a possible example, the second subset 1010 may form a complete ring, similar to the first subset 1002, such that the first subset 1002 and the second subset 1010 may be substantially similar. In an example, a first winding of the one or more additional windings of the second subset 1010 may be wound around a second center axis (e.g., the y-axis). In some examples, the second center axis may be substantially perpendicular to the center axis.

The segments of the second subset 1010 may be substantially similar to the segments of the first subset 1002. For example, the segments of the second subset 1010 may comprise a support structure (e.g., support structure 302), a core element (e.g., core element 350), an attachment structure (e.g., the attachment structure 396), a front attachment structure (e.g., the front attachment structure 3002), etc.

The second subset 1010 may comprise second inductive elements 1012. In the illustrated example, the second inductive elements 1012 may be substantially similar to the inductive elements 3000 illustrated with respect to FIGS. 8 and 9. For example, the second inductive elements 1012 may comprise the first inductive portions 806, which can be received within a core channel of a core element, and the second inductive portions 808, which may not be received within the core channel. In this way, the second inductive elements 1012 can be wound around the segment of the second subset 1010 in a similar manner as illustrated with respect to FIGS. 8 and 9.

It will be appreciated that any number of second inductive elements 1012 (e.g., one or more) are envisioned, though in the illustrated example of FIG. 10, the second inductive elements 1012 comprise two inductive elements. The second inductive elements 1012 may extend through the support structures of the second subset 1010 of segments 1000, such that the second inductive elements 1012 can be arranged to form a partial ring. The second inductive elements 1012 can be maintained in place with respect to the support structures and core elements of the second subset 1010 of segments 1000 in a similar manner as described with respect to FIGS. 3 to 8.

The second inductive elements 1012 of the second subset 1010 can define a second winding 1014 of the transformer. In an example, the second winding 1014 may comprise a primary winding or a secondary winding. For example, when the first winding 1006 of the first subset 1002 comprises the primary winding, the second winding 1014 of the second subset 1010 may comprise the secondary winding. In another example, when the first winding 1006 of the first subset 1002 comprises the secondary winding, the second winding 1014 of the second subset 1010 may comprise the primary winding. In an example, the second subset 1010 may comprise a first segment having a first inductive element that defines a first additional winding. The second subset 1010 may comprise a second segment having a second inductive element defining a second additional winding. In some examples, the first additional winding and the second additional winding may be inductively coupled with the first winding 1006.

In operation, power may be applied to one of the inductive elements. For example, when power is applied to the first inductive elements 1004, an inductive field may be generated. This inductive field can induce a current in the second inductive elements 1012. In another example, when power is applied to the second inductive elements 1012, an inductive field may be generated. This inductive field can induce a current in the first inductive elements 1004. It will be appreciated that this transfer of power between the first inductive elements 1004 and the second inductive elements 1012 will generate magnetic fields, or magnetic flux, that may be shunted by (e.g., confined within) the core element 350. The magnetic flux may escape the core element 350 in the vicinity of a core airgap (e.g., the airgap that separates the rotor from the stator and allows the rotor to rotate relative to the stator).

Assembly and/or disassembly of portions of the power coupling device 200 may be relatively easy due to the segments 1000. For example, the segments 1000 can be assembled by inserting the core element 350 into the openings of the support structure 302, and inserting the inductive elements into the core channel 356 of the core element 350. The inductive elements and the core element 350 may be held in place with respect to the support structure 302 by attaching the attachment structure 396 and the front attachment structure 3002 to the support structure. With a segment 1000 partially or fully assembled, the segment can be attached to neighboring segments by way of the first attachment portions 336 and the second attachment portions 338. Segments 1000 can likewise be readily disassembled and taken apart, for reasons due to maintenance, replacement, etc.

The words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

What is claimed is:

1. A power coupling device configured to transfer power between a stator and a rotor, the power coupling device comprising:
    a support structure defining an opening;
    a core element comprising a ferrite material, the core element configured to be received within the opening of the support structure, the core element defining a core channel, the core channel having:
        a first channel portion having a first channel width measured along a second axis that is substantially perpendicular to the first axis; and
        a second channel portion having a second channel width measured along the second axis, the first channel width different than the second channel width;
    an inductive element configured to be received within the core channel; and
    an attachment structure removably attached to the support structure, the attachment structure configured to attach the core element to the support structure, the core element disposed between the support structure and the attachment structure,
    wherein a support member of the support structure configured to be received within the first channel portion of the core channel.

2. The power coupling device of claim 1, the inductive element facing a first side of the core element, the attachment structure facing a second side of the core element.

3. The power coupling device of claim 1, the core channel of the core element extending along a first axis between a first end and a second end of the core element.

4. The power coupling device of claim 1, the inductive element configured to be received within the second channel portion of the core channel, the support member of the support structure disposed between the core element and the inductive element.

5. The power coupling device of claim 4, a front attachment structure removably attached to the support structure diametrically opposed to the attachment structure, the inductive element disposed between the front attachment structure and the support member of the support structure.

6. A segmented power coupling device comprising a plurality of segments configured to transfer power between a stator and a rotor, the segmented power coupling device comprising:
  a segment comprising:
    a support structure defining multiple openings;
    a core element comprising a ferrite material and defining a first side and a second side, the core element configured to be received within the multiple openings of the support structure, the core element defining a core channel defined along the first side; and
    an inductive element configured to be at least partially received within the core channel and wound around the core element from the first side to the second side,
    wherein a support member of the support structure configured to be received within the first channel portion of the core channel.

7. The segmented power coupling device of claim 6, a first subset of the plurality of segments arranged to define a ring.

8. The segmented power coupling device of claim 7, a plurality of first inductive elements of the first subset coupled in parallel to define a first winding of a transformer.

9. The segmented power coupling device of claim 8, a second subset of the plurality of segments arranged to define a partial ring.

10. The segmented power coupling device of claim 9, one or more second inductive elements of the second subset defining a second winding of the transformer.

11. The segmented power coupling device of claim 9, the second subset of the plurality of segments forming one of the stator or the rotor.

12. The segmented power coupling device of claim 6, the inductive element having a first inductive portion and a second inductive portion, the first inductive portion received within the core channel, the second inductive portion not received within the core channel.

13. A power coupling device configured to transfer power between a stator and a rotor, the power coupling device comprising:
  a support structure defining a support member and an opening;
  a core element comprising a ferrite material and configured to be received within the opening of the support structure, the core element defining a core channel and the support member of the support structure configured to be received within the core channel; and
  an inductive element configured to be received within the core channel, wherein the support member of the support structure is disposed between the inductive element and the core element along a back face of the core element.

14. The power coupling device of claim 13, the core element defining a first side and a second side, the first side of the core element facing the support structure, the second side of the core element facing away from the support structure.

15. The power coupling device of claim 14, the first side of the core element defining a plane, the back face of the core element extending substantially parallel to the plane and spaced a first distance apart from the plane.

16. The power coupling device of claim 15, the core element having an intermediate face defining the core channel and extending substantially parallel to the back face, the intermediate face spaced a second distance apart from the plane, wherein the first distance is greater than the second distance.

17. The power coupling device of claim 16, the intermediate face defining an intermediate plane, the inductive element disposed on a first side of the intermediate plane, the support member of the support structure disposed on a second side of the intermediate plane.

18. The power coupling device of claim 13, a front attachment structure removably attached to the support structure, the inductive element disposed between the front attachment structure and the support member of the support structure.

* * * * *